United States Patent
Kim

(10) Patent No.: US 10,912,664 B2
(45) Date of Patent: Feb. 9, 2021

(54) STENT WITH INDUCTION RESPONSIVE MUSCLES THAT FACILITATE IMPLANTATION ADJUSTMENTS

(71) Applicant: Cook Medical Technologies LLC, Bloomington, IN (US)

(72) Inventor: Woong Kim, West Lafayette, IN (US)

(73) Assignee: Cook Medical Technologies, LLC, Bloomington, IN (US)

( * ) Notice: Subject to any disclaimer, the term of this patent is extended or adjusted under 35 U.S.C. 154(b) by 148 days.

(21) Appl. No.: 16/164,180

(22) Filed: Oct. 18, 2018

(65) Prior Publication Data

US 2019/0151122 A1 May 23, 2019

Related U.S. Application Data

(60) Provisional application No. 62/588,992, filed on Nov. 21, 2017.

(51) Int. Cl.
| | |
|---|---|
| *A61F 2/86* | (2013.01) |
| *A61F 2/24* | (2006.01) |
| *A61F 2/07* | (2013.01) |
| *A61F 2/915* | (2013.01) |

(52) U.S. Cl.
CPC ............ *A61F 2/86* (2013.01); *A61F 2/07* (2013.01); *A61F 2/2418* (2013.01); *A61F 2/915* (2013.01); *A61F 2210/0014* (2013.01); *A61F 2210/0019* (2013.01); *A61F 2210/0038* (2013.01); *A61F 2210/0066* (2013.01); *A61F 2250/0001* (2013.01); *A61F 2250/001* (2013.01); *A61F 2250/0042* (2013.01)

(58) Field of Classification Search
CPC ...................................................... A61F 2/82
See application file for complete search history.

(56) References Cited

U.S. PATENT DOCUMENTS

| | | | |
|---|---|---|---|
| 5,562,641 | A | 10/1996 | Flomenblit et al. |
| 6,077,298 | A | 6/2000 | Tu et al. |
| 6,579,297 | B2 | 6/2003 | Bicek et al. |
| 7,658,761 | B2 | 2/2010 | Yamauchi et al. |

(Continued)

FOREIGN PATENT DOCUMENTS

WO 2011067764 6/2011

OTHER PUBLICATIONS

European Patent Office, European Search Report for Application No. 18207621.6, Published Feb. 4, 2019, Munich Germany.

(Continued)

*Primary Examiner* — Jacqueline Woznicki
(74) *Attorney, Agent, or Firm* — Liell & McNeil

(57) ABSTRACT

A stent has a tubular shaped framework that includes a plurality of vertices that are each defined by a pair of struts. A plurality of induction responsive muscles are associated, respectively, with one of the plurality of vertices by being attached to each strut of a pair of struts. The induction responsive muscles have a relaxed state at body temperatures, and have a contracted state at an elevated temperature greater than body temperature. If the stent has an initial unsatisfactory implant orientation or position or other expansion irregularity, the application of an electromagnetic induction field may be applied to temporary 11 reduce the diameter of the stent to adjust its positioning and/or orientation.

14 Claims, 5 Drawing Sheets

(56) References Cited

U.S. PATENT DOCUMENTS

| | | | |
|---|---|---|---|
| 8,043,354 B2 | 10/2011 | Greenberg et al. | |
| 9,180,005 B1* | 11/2015 | Lashinski | A61F 2/2466 |
| 2002/0138134 A1 | 9/2002 | Kim et al. | |
| 2006/0161244 A1* | 7/2006 | Seguin | A61F 2/07 |
| | | | 623/1.23 |
| 2006/0184231 A1 | 8/2006 | Rucker | |
| 2006/0211984 A1 | 9/2006 | Blank et al. | |
| 2007/0073380 A1 | 3/2007 | Vazquez et al. | |
| 2008/0004692 A1 | 1/2008 | Henson et al. | |
| 2008/0009931 A1* | 1/2008 | Bartning | A61F 2/005 |
| | | | 623/1.1 |
| 2008/0275548 A1* | 11/2008 | Svensson | A61F 2/07 |
| | | | 623/2.1 |
| 2013/0018452 A1* | 1/2013 | Weitzner | A61F 2/915 |
| | | | 623/1.15 |
| 2013/0046373 A1* | 2/2013 | Cartledge | A61F 2/2439 |
| | | | 623/1.11 |
| 2013/0166017 A1* | 6/2013 | Cartledge | A61F 2/2439 |
| | | | 623/1.15 |
| 2013/0331927 A1 | 12/2013 | Zheng et al. | |
| 2014/0324154 A1* | 10/2014 | Shalev | A61F 2/82 |
| | | | 623/1.13 |
| 2015/0073319 A1 | 3/2015 | Holschuh et al. | |
| 2015/0135506 A1* | 5/2015 | White | A61F 2/2415 |
| | | | 29/428 |
| 2018/0008409 A1* | 1/2018 | Kutzik | A61F 2/2445 |
| 2018/0104077 A1* | 4/2018 | Cartledge | A61F 2/2439 |
| 2018/0147059 A1* | 5/2018 | Hammer | A61F 2/2418 |
| 2018/0368965 A1* | 12/2018 | Janardhan | A61B 17/12163 |

OTHER PUBLICATIONS

Müller et al., Electromagnetic Induction Heating of an Orthopaedic Nickel—Titanium Shape Memory Device, Journal of Orthopaedic Research, Dec. 2010, pp. 1671-1676, Germany.

* cited by examiner

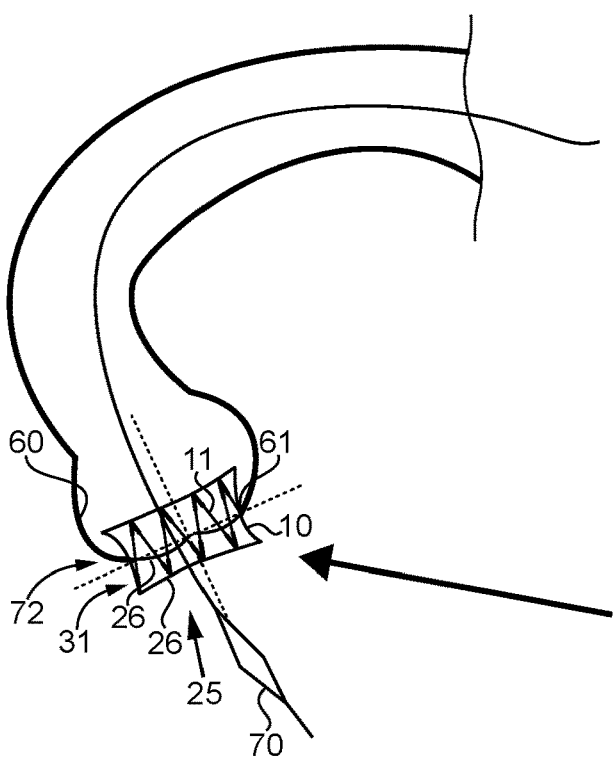
FIG. 11
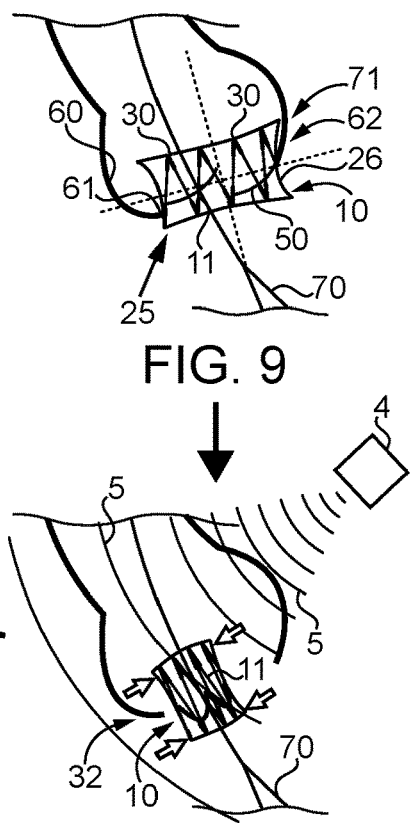
FIG. 9
FIG. 10
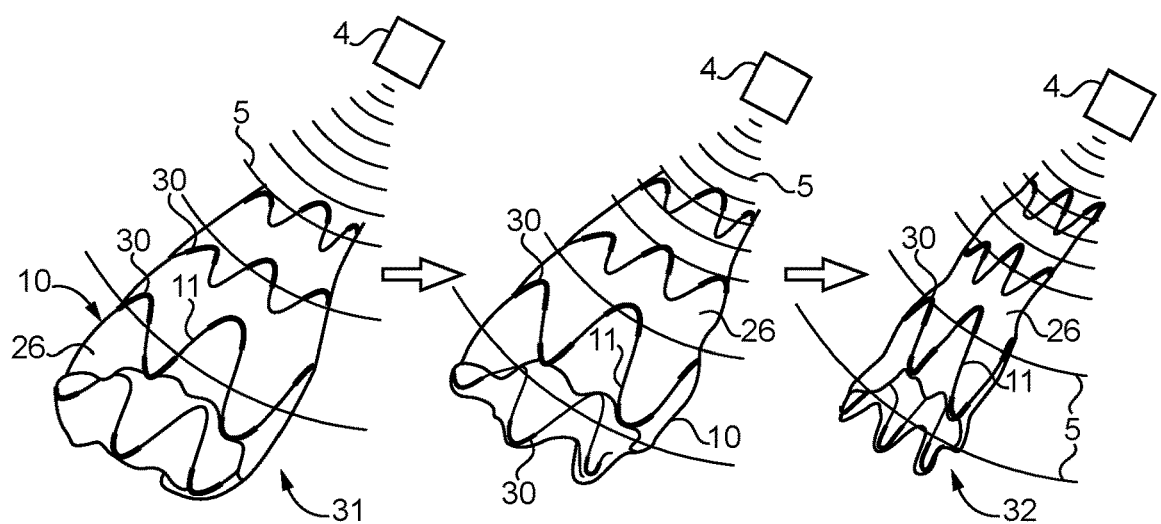
FIG. 12

STENT WITH INDUCTION RESPONSIVE MUSCLES THAT FACILITATE IMPLANTATION ADJUSTMENTS

TECHNICAL FIELD

The present disclosure relates generally to stents, and more particularly to induction responsive muscles that can facilitate adjustment of orientation and/or position of a stent during and after a delivery procedure.

BACKGROUND

Almost all current endovascular devices exclusively rely on the elastic radial force from stents that are often stitched into a graphed device to expand to the inner diameter of a vessel, and then fixate. For this reason, once the device has been partially or fully deployed from a delivery system, the released devices are prone to suddenly expand and jump to a delivery position in contact with a vessel wall. Even when the delivery device is precisely located, the jumping of the device may result in an incorrect landing of the device by either position, relative to the vessel and/or angle of the mouth or sealing segment of the stent, as well as uneven deployment of the landing stent with irregular peak/to/peak distances. One attempt at addressing this problem is to include releasable ties or the like to slow the expansion of the stent during the delivery process. Nevertheless, even with these improvements, there remains a risk of suboptimal deployment, and these strategies do not provide an option to undue a current stent landing to allow for readjustment of the stent orientation, positioning and/or irregular expansion shape.

The present disclosure is directed toward one or more of the problems set forth above.

SUMMARY

In one aspect, a stent has a tubular shaped framework that includes a plurality of vertices that are each defined by a pair of struts. Each of a plurality of induction responsive muscles is associated with one of the plurality of vertices by being attached to each strut of the pair of struts. Each of the induction responsive muscles has a relaxed state at temperatures less than 37° C., and has a contracted state at a temperature greater than 37° C. Each of the induction responsive muscles reduces an angle of a respective one of the vertices responsive to changing from the relaxed state to the contracted state. A diameter of the tubular shaped framework is reduced responsive to a collective effect of the plurality of induction responsive muscles changing from the relaxed state to the contracted state.

In another aspect, a method of implanting a stent includes moving the stent in a contracted configuration to a deployment area in a passageway. The stent is changed from the contracted configuration to a deployed configuration in a first arrangement with a wall defining the passageway. The stent is this contracted from the deployed configuration toward the contracted configuration by immersing the stent in an electromagnetic induction field. At least one of an orientation and a position of the stent is adjusted. The stent is then expanded back to the deployed configuration in a second arrangement, which is different from the first arrangement, with the wall defining the passageway at least in part by ceasing the immersion of the stent in the electromagnetic induction field. The contracting step includes changing the induction responsive muscles from a relaxed state to a contracted state. The expanding step includes changing the induction responsive muscles from the contracted state to the relaxed state.

BRIEF DESCRIPTION OF THE DRAWINGS

FIG. 9 is a schematic view of a stent that includes an artificial heart valve implanted with a suboptimal orientation;

FIG. 10 is a schematic view of the stent from FIG. 9 contracting responsive to immersion in an electromagnetic induction field;

FIG. 11 shows the stent of FIGS. 9 and 10 expanded back to a deployment configuration with an adjusted orientation relative to that of FIG. 9;

FIG. 12 shows a series of perspective illustrations of a sealing end of a stent contracting responsive to immersion and an electromagnetic induction field according to the present disclosure;

DETAILED DESCRIPTION

Figure 1:
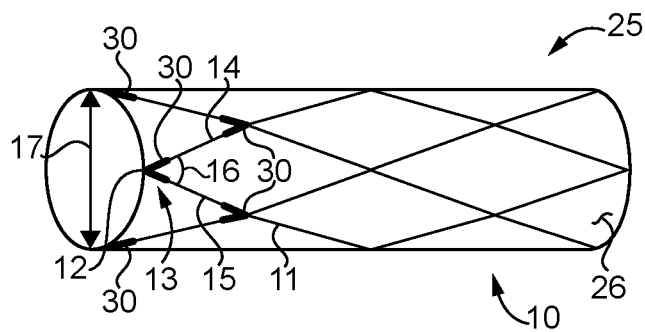
FIG. 1 is a perspective schematic view of a stent in a deployed configuration according to the present disclosure.
Figure 2:
FIG. 2 is a perspective schematic view of the stent of FIG. 1 in a contracted configuration.
Figure 3:
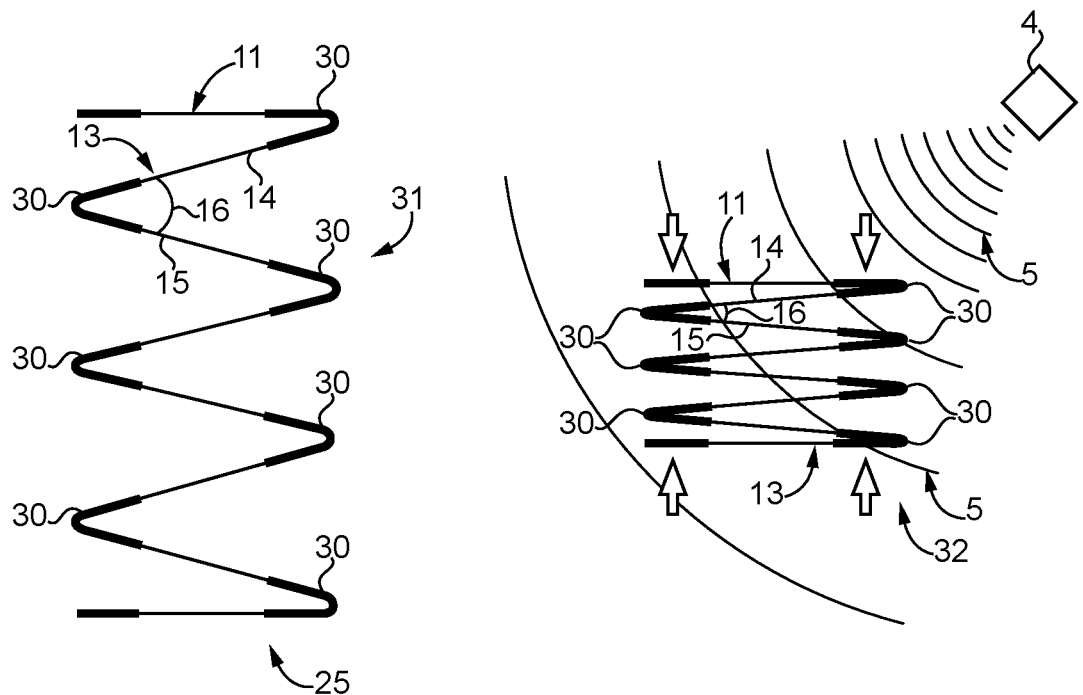
FIG. 3 is a schematic view of a portion of a tubular framework from the stent of FIG. 1 in a deployed configuration.
Figure 4:
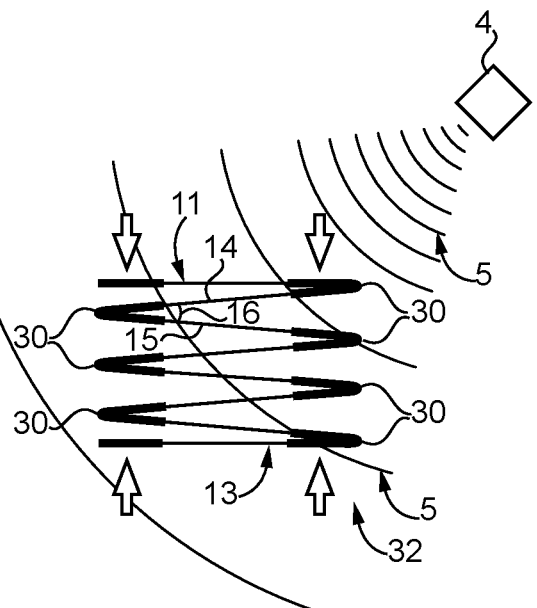
FIG. 4 shows the framework fragment of FIG. 3 contracted responsive to being immersed in an electromagnetic induction field.

Referring initially to FIGS. 1-4, a stent 10 includes a tubular shaped framework 11 with a plurality of vertices 12 that are each defined by a pair of struts 13. Each of a plurality of induction responsive muscles 30 are attached to respective pairs of struts 13. Each of the induction responsive muscles 30 is associated with one of the plurality of vertices 12 by being attached to each strut 14 and 15 of the pair of struts 13. Each of the induction responsive muscles 30 has a relaxed state 31 at temperatures less than 37° C., and has a contracted state 32 at a temperature greater than 37° C. In this way, the muscles preferably assume the relaxed state 31 at normal body temperatures, but will assume the contracted state if heated to a temperature greater than 37° C. Those skilled in the art will appreciate that the contracted state temperature can be engineered to a suitable temperature. Each of the induction responsive muscles 30 reduces an angle 16 of a respective one of the vertices 12 responsive to changing from the relaxed state 31 to the contracted state 32. The plurality of the induction responsive muscles 30 are distributed around stent 10 such that a diameter 17 of the tubular shaped framework 11 is reduced responsive to a collective effect of the plurality of induction responsive muscles 30 changing from the relaxed state 31 to the contracted state 32. Also, in most instances, the individual induction responsive muscles 30 will be out of contact with each other. Those skilled in the art will appreciate that the stent 10 may have a conventional design shaped from nitinol or stainless steel wire bent back and forth into a z-shaped pattern around the periphery of the tubular shaped framework 11. Nevertheless, any alloy or suitable plastic may be utilized for the stent of the present disclosure. Although not necessary, in many cases of a stent 10 according to the present disclosure, a fabric tube 26 may be attached to the tubular shaped framework 11 in a suitable manner, such as by sutures. The fabric tube 26 may be any fabric known in the art including textiles and/or plastic sheeting of a suitable type.

Referring now in addition to FIGS. 5-8, induction responsive muscles 30 according to the present disclosure can take a variety of forms, and be at least partially constructed from shape memory materials, such as nitinol. In each case, the induction responsive muscles 30 are set to have the contracted state 32 at a higher Af temperature than body temperature, and can be placed in attachment on the conventional underlying stent via sleeving or possibly low temperature soldering, adhesives, mechanical connections, or any other suitable attachment strategy. In a deployed state within a vessel, the induction responsive muscles 30 are engineered to assume the relaxed state 31 of the low stiffness martensitic phase. However, once a magnetic induction field is applied, such as from outside of the body, the temperature of the induction responsive muscles 30 will rise beyond that of the Af temperature, and the shape memory alloy elements of the induction responsive muscles 30 transform into a stiffer austenitic phase that is accompanied by a shape change. With the preprogrammed contracted state 32 associated with the austenite phase, the induction responsive muscles 30 apply a gripping force upon the stent 10 and reduce its diameter 17, such as to facilitate readjustment at a deployment site within the body.

Figure 5:
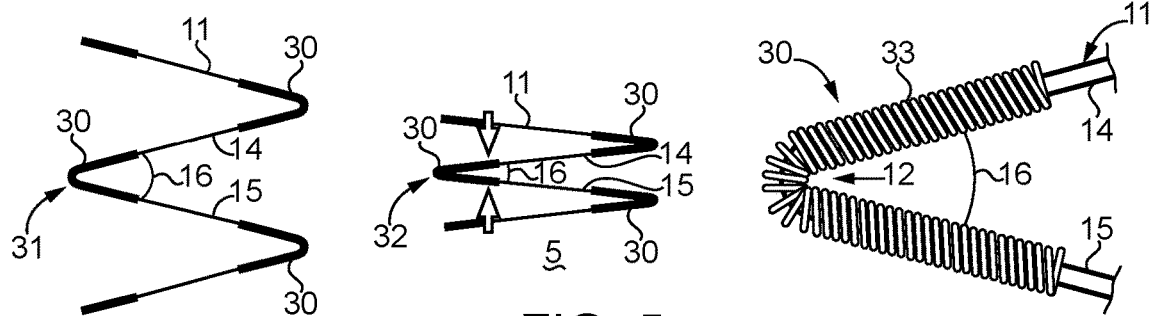
FIG. 5 is a side schematic view of an spring sleeve version of an induction responsive muscles according to the present disclosure attached to two struts of the framework for the stent of FIG. 1.

FIG. 5 shows an example induction responsive muscle 30 in the form of a spring sleeve 33 with an internal diameter sized to receive the wire that defines struts 14 and 15. Each of the induction responsive muscles 30 in the form of a spring sleeve 33 may be positioned on the wire out of which the tubular framework 11 is formed. Each induction responsive muscle 30 is preferably formed of a suitable shape memory alloy known in the art, including but not limited to nitinol, which may be the same or a different alloy that is used to form the individual struts 14 and 15 of the tubular shaped framework 11 of stent 10. The far left image shows the induction responsive muscle 30 in the relaxed state 31, and the middle image shows the contracted state 32.

Figure 6:
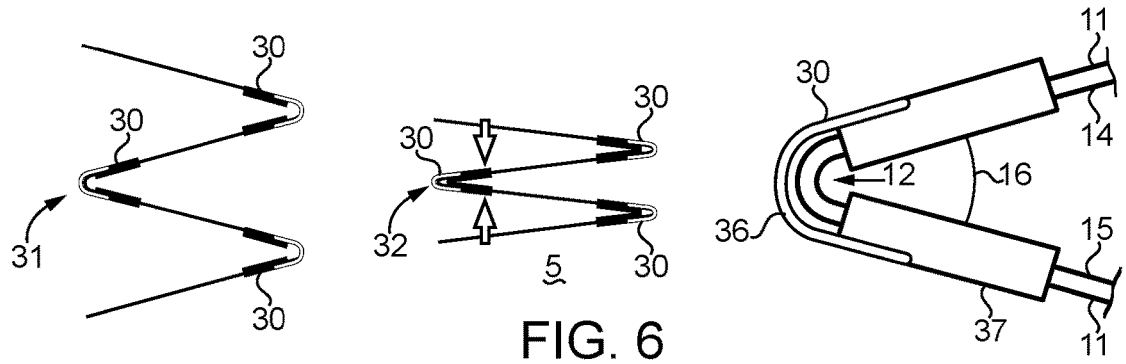
FIG. 6 is a side schematic view of an living hinge version of an induction responsive muscle according to another aspect of the present disclosure attached to two struts of the framework for the stent of FIG. 1.

FIG. 6 shows an alternative strategy in which the induction responsive muscles 30 each include a living hinge 36 that is attached to the individual struts 14 and 15, such as via a non-shape memory alloy sleeve. Alternatively, the ends of the living hinge 36 may be welded onto the individual struts 14 and 15. Thus, in the version of FIG. 6, each of the induction responsive muscles 30 includes a living hinge 36 of a shape memory material attached to a strut connector 37 of a material different from the shape memory material. Strut connectors 37 may be slid onto the wire used to make tubular shaped framework 11 generally and struts 14 and 15 particularly at the time that the stent 10 is shaped. Alternatively, the strut connectors 37 may be attached after formation of the stent 10 in a suitable manner, such as by welding or maybe by snap connecting the individual strut connectors onto the struts 14 and 15.

Figure 7:
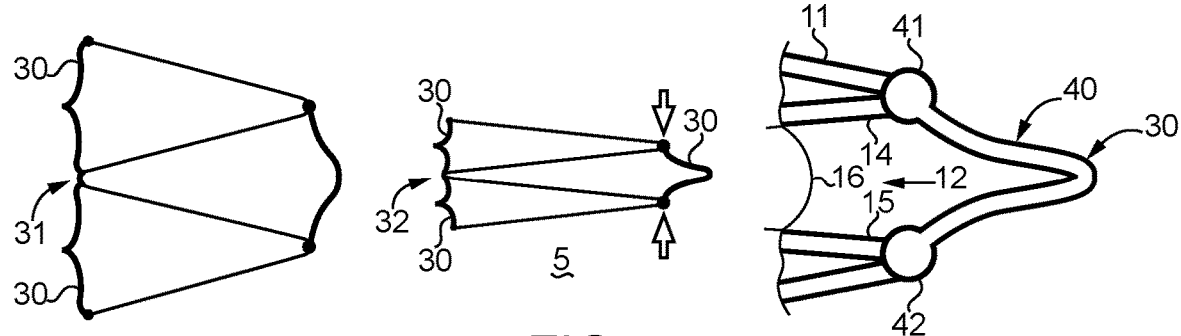
FIG. 7 shows a schematic view of a single bend bridge version of an induction responsive muscle attached to two struts of the framework for the stent of FIG. 1.
Figure 8:
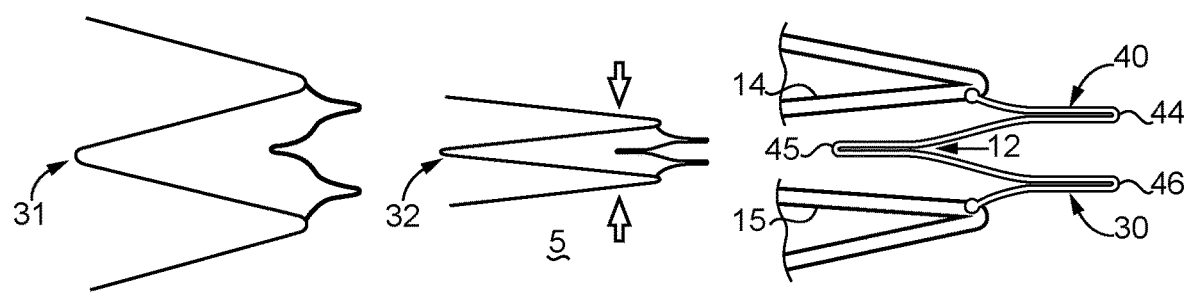
FIG. 8 is a side schematic view of a three bend bridge version of an induction responsive muscle attached to two struts of the framework of the stent of FIG. 1.

The induction responsive muscles 30 may also take the form of a bridge 40 with one end 41 attached to one strut 14 of the pair of struts, and an opposite end 42 attached to another strut 15 of the pair of struts. This attachment, for instance may be accomplished by welds or any other suitable strategy. In the embodiment of FIG. 7, the bridge 40 includes exactly one bend 43 between ends 41 and 42. The embodiment of FIG. 8 shows a plurality of bends between the ends 41 and 42. In particular, the embodiment of FIG. 8 shows a bridge 40 with a first bend 44, a second bend 45 and a third bend 46. In both FIGS. 7 and 8, the far left image shows the induction responsive muscle 30 in the relaxed state 31, and the middle image shows the contracted state 32.

The present disclosure applies particularly to stents 10 requiring precise placement either by position and or orientation in order to produce desired outcome for a patient. Thus, a stent 10 according to the present disclosure could include an artificial heart valve, or a covered stent with one or more fenestrations or maybe even a covered stent with one entrance opening and two exit openings of the type utilized for treatment of abdominal aortic aneurysms. Those skilled in the art will recognize other stent applications, fabric covered or not, that could benefit from the induction responsive muscles 30 of the present disclosure that will permit the stent to be expanded at a deployment site, and then contracted via the induction responsive muscles to reduce the diameter of the stent temporarily to readjust its position and orientation. In most applications, the tubular framework 11 of the stent 10 will have a self expanding bias toward a deployed configuration 25 as shown in FIG. 1. The induction responsive muscles 30 act in opposition to, and overcome, the self expanding bias of the tubular shaped framework 11 when the induction responsive muscles are changed from the relaxed state 31 to the contracted state 32.

INDUSTRIAL APPLICABILITY

The present disclosure finds applicability in any instance where a stent is implanted within a passageway. The present disclosure finds particular applicability to stents having a self expanding bias tubular shaped framework, and maybe even more particularly to covered stents. The present disclosure finds particular applicability to stents that are sensitive to implantation irregularities due to position and/or orientation and/or other expansion irregularities that could undermine the desired outcome of the stent implantation.

Referring now to FIGS. 9-11, portions of an example procedure for implanting an artificial heart valve 50 utilizing a stent 10 according to the present disclosure is illustrated. In this example, the stent 10 includes a single band of wire formed in a zigzag pattern into a self expanding tubular shaped framework 11 that is attached to a fabric tube 26. In this case, stent 10 includes an artificial heart valve 50 that is positioned within, and attached to, the tubular framework 11. The procedure starts at FIG. 9 where the stent has already been implanted at the correct location, but with a slight mis-adjustment in orientation so that the artificial heart valve performs in a manner that is less than optimal. In particular, FIG. 9 shows stent 10 positioned in a passageway 60 and in contact with a wall 61 in a deployed configuration 25 in a first arrangement 71. At this point in the procedure, the stent 10 is still connected to a deployment device 70, such as by one or more release wires or sutures of a type known in the art. After visual imaging or some other test confirms that the stent has a suboptimal orientation at the deployment area 62, the physician may then decide to exercise the induction responsive muscles 30 incorporated into stent 10 in order to move the stent from the deployed configuration 25 toward a contracted configuration responsive to immersing the stent 10 in an electromagnetic induction field 5. For instance, an electromagnetic field generator 4 may be positioned outside of a patient, which may be real or artificial, and may generate a rapidly changing electromagnetic induction field 5 that increases the temperature of the induction responsive muscles 30 either directly and/or indirectly by heat generated by eddy currents in the underlying tubular framework 11 or in the muscles 30 themselves, or both. The stent 10 responds by contracting and reducing its diameter, which may result in the stent coming completely out of contact with the wall 61. The user may then slightly adjust the positioning and orientation of stent 10, terminate the electromagnetic induction field 5 and allow the induction responsive muscles 30 to cool back toward body temperature (37° C.) to change from the contracted state 32 described earlier toward returning to the relaxed state 31 as shown in FIG. 11, with stent 10 now in a second arrangement 72 with the wall 61. As the induction responsive muscles 30 relax, the self expanding nature of the underlying tubular framework 11 tends to expand the stent 10 back out toward contact with the wall 61 of the passageway 60. The physician may then confirm that the stent 10 is now acceptably placed and orientated for the proper functioning of the artificial heart valve 50. Thereafter, the deployment device 70 may be disconnected from stent 10 and withdrawn from the passageway 60 in a known manner. The connective features between the deployment device 70 and stent 10 are not shown, but are well known, and could include one or more wires or control lines. Those skilled in the art will appreciate that the term "passageway" as used in the present disclosure typically refers to a passageway within a patient, but can refer to artificial passageways that may be used for demonstrating the stent of the present disclosure, or for teaching purposes without departing from the present disclosure. Thus, all of the methods of using the stent 10 taught in this disclosure refer to both real and artificial passageways in live and artificial bodies, respectively.

Referring now to FIG. 12, three views of the stent 10 from FIG. 1 are shown. When one moves from left to right and the stent 10 is immersed in the electromagnetic induction field 5 generated by field generator 4, the induction responsive muscles 30 change from a relaxed state 31 toward a contracted state 32 in moving from left to right. When the electromagnetic induction fields is terminated, the induction responsive muscles 30 change from the contracted state 32 toward the relaxed state, and the stent resiliently expands back toward a deployed configuration 25 that is shown in the left side picture as the induction responsive muscles cool toward body temperature, or 37° C., and the self expanding bias overcomes the induction responsive muscles 30.

Figure 13:
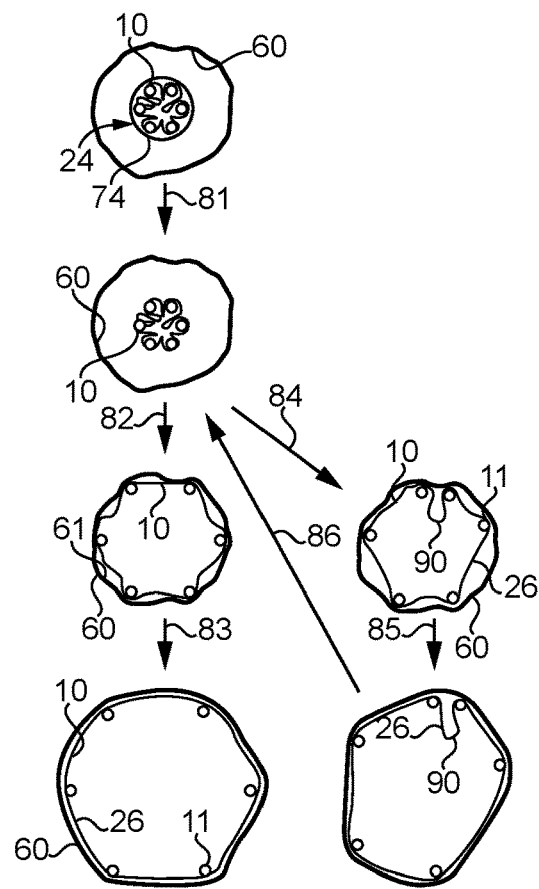
FIG. 13 shows a series of schematic end views in the delivery of the stent to a passageway that initially includes an in-fold complication followed by contraction of the stent according to the present disclosure and then re-expanding the stent with an improved vessel wall contact.

Referring now to FIG. 13, an end view showing the deployment of a stent 10 in a passageway 60 starts at the top image with the stent 10 held in a contracted state 24 by a sheath 74 while being maneuvered to a deployment area 62 in passageway 60. Following arrow 81 to the next image, the sheath 74 is removed in the first step toward the deployment of the stent 10, which is now no longer constrained by sheath 74. In some instances, following arrow 84 to another image, a complication may develop as the stent 10 resiliently self expands toward contact with the vessel wall 61. In this case, an in-fold 90 in the fabric tube cover 26 attached to tubular shaped framework 11 occurs. As the stent 10 continues to expand, as shown by image pointed to by the arrow 85, the in-fold 90 remains, and may be discovered using visualization and/or leak detection strategies. For instance, the in-fold 90 could cause an endoleak, if the stent 10 was being used, for instance, to span an aneurism. After the improper implantation is discovered, an electromagnetic induction field (not shown) may be applied to stent 10 such that following arrow 86 to a previous image, the stent 10 reduces in diameter in an attempt to redeploy the stent without an in-fold 90. Thereafter following arrow 82 downward to another image, the stent 10 expands back out into contact with wall 61 of passageway 60. Then following arrow 83 to the bottom left image, the stent 10 becomes fully expanded and properly configured as the induction responsive muscles cool toward the relaxed state temperature 37° C. Those skilled in the art will appreciate that in many instances, no problems will occur and the deployment will simply follow arrows 81, 82, and 83 to a final proper deployment. However, by detecting a less than optimal deployment, as per the complications associated with the images associated with arrows 84 and 85, the induction responsive muscles 30 of the present disclosure provide a strategy for reducing the diameter of the stent 10, making necessary adjustments and then allowing a self expanding biasing stent 10 to gradually overcome the contraction of the induction responsive muscles as the electromagnetic induction field is terminated and the stent 10 and its inductive responsive muscles 30 cool.

Figure 14:
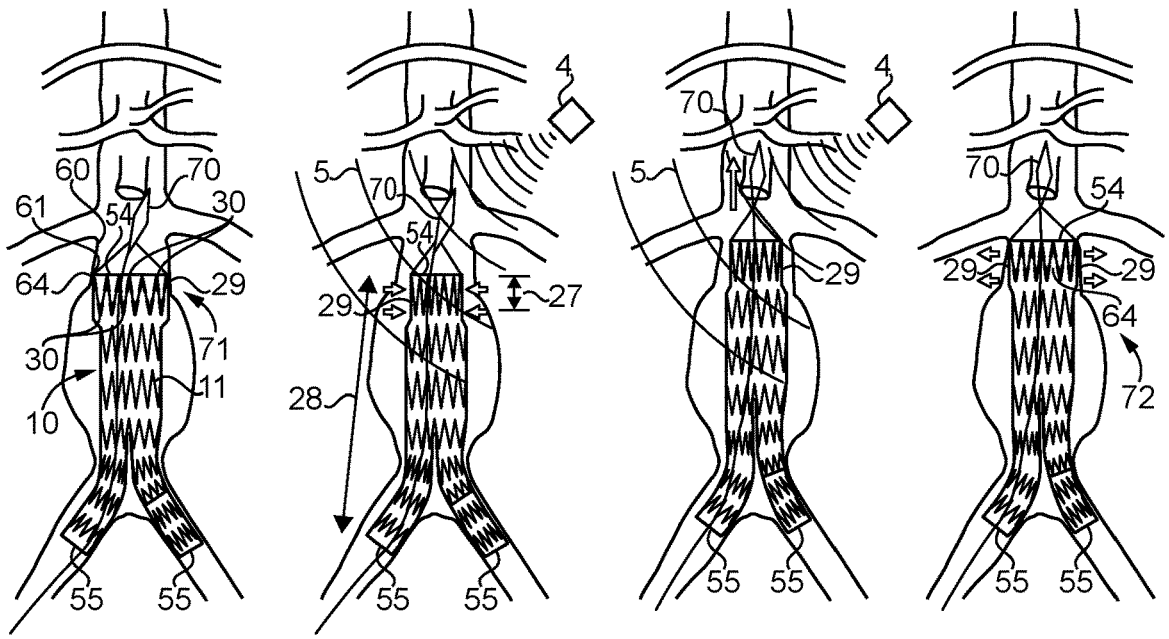
FIG. 14 is a schematic view showing an abdominal aortic aneurism repair with a stent initially implanted with suboptimal placement followed by contraction of a sealing segment of the stent according to the present disclosure and then re-expansion at an improved stent sealing position.

Referring now to FIG. 14, a series of four images show the implantation of a stent 10 in the form of an AAA graph with an initial sub-optimal placement followed by adjusting the position of the stent to a more desired location as per the present disclosure. In the left most image, the sealing segment of stent 10 has only a small area of contact 64 with wall 61 inviting a potential endoleak into the aneurism. Thus, the first or left most image represents the stent 10 being deployed in a first arrangement 71 with wall 61 of passageway 60. Although obviously apparent, stent 10 includes exactly one entrance opening 54 and two exit openings 55 corresponding to the iliac arteries. In this case, a minority 27 of length 28 of the fabric tub 26 can be considered to be a sealing segment 29. After recognizing that the sealing segment 20 has a less than ideal contact with the wall 61 of passageway 60, the physician may choose to use an electromagnetic field generator 4 to immerse stent 10 in an electromagnetic induction field 5 to generate heat in the induction responsive muscles 30 and cause the sealing segment 29 of the stent 10 to contract as shown in the second image from the left. Thus, in this example, the stent 10 may include induction responsive muscles 30 only in the region of the sealing segment 29 rather than throughout the stent as in the previously described versions. After shrinking the diameter of the sealing segment 29, the deployment device 70, which is still connected to the stent 10, is utilized to maneuver the stent 10 for better placement as shown in the third image. Thereafter, the electromagnetic induction field may be terminated allowing the induction responsive muscles 30 in the sealing zone 29 to cool toward body temperature and move to their relaxed state 31 allowing the self expanding bias of the stent 10 to assume a second arrangement 72 with respect to the wall 61 of passageway 60 as shown in the far right image. In this better seating, the sealing segment 29 has a greater area of contacts 64 with the wall 61 of passageway 60 to better prevent endoleaks into the aneurism below. Thereafter, the remaining portions of the aortic aneurism treatment may continue in a manner known in the art. However, those skilled in the art will appreciate that if even after the second deployment the stent expands to a less than optimal positioning and orientation, the procedure of immersing the stent in the electromagnetic induction field can be repeated, another adjustment can be made, and then the induction responsive muscles are allowed to cool. This procedure can be repeated any number of times until the stent 10 is satisfactorily positioned in the passageway 60.

Figure 15:
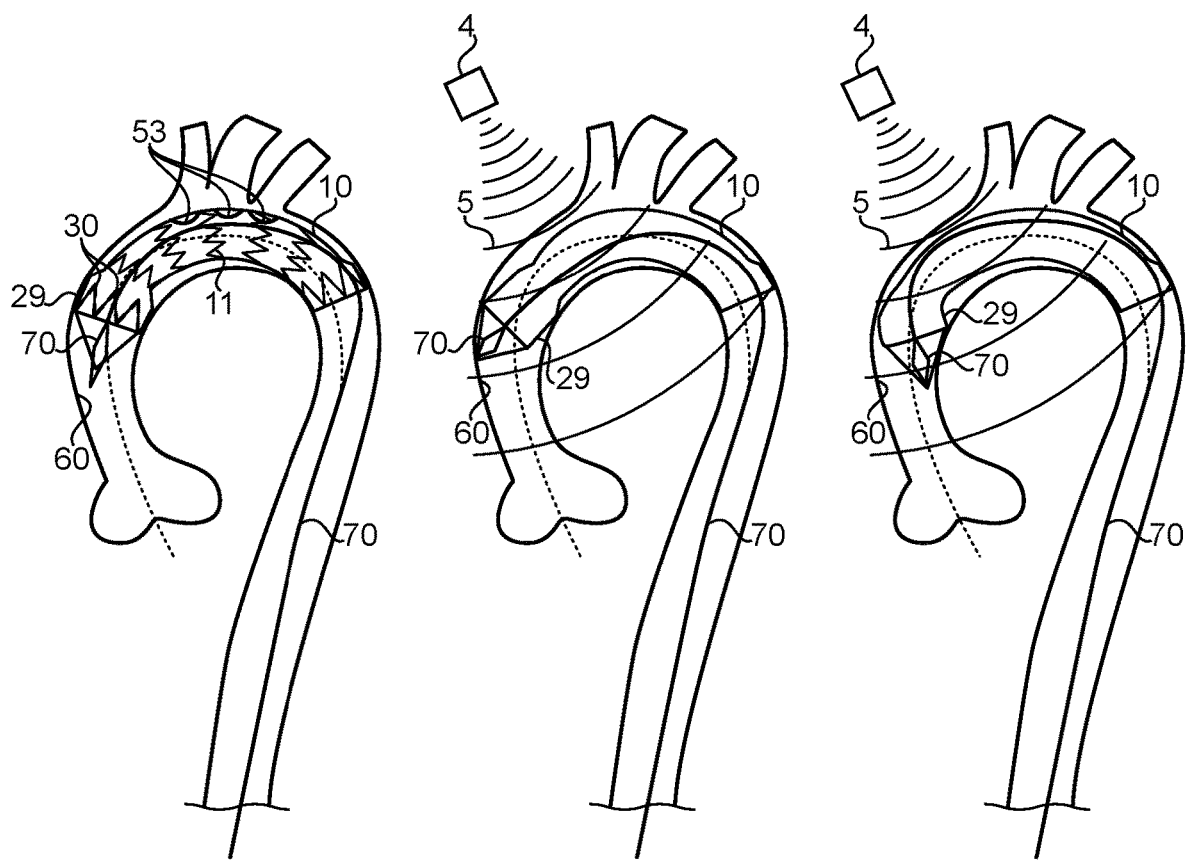
FIG. 15 shows a proper implantation orientation and positioning to the left followed by two unsatisfactory deployments that can be adjusted to the proper implantation orientation according to the present disclosure.

Referring now to FIG. 15, three images showing a stent 10 according to the present disclosure deployed with ideal sealing in the first or left most image, and with unsatisfactory sealing in the second and third image due to the improper orientation of one end of the stent 10. Those skilled in the art will appreciate that when the stent 10 has one of the unsatisfactory sealing arrangements of the second two images is immersed in the electromagnetic induction field 5 from the electromagnetic field generator 4, the deployment device 70 may be used to adjust the orientation of the stent end toward the more ideal sealing configuration shown in the first image. This sequence is also of interest for showing that the stent 10, which may include a fabric tube covering 26, may have fenestrations 53 to accommodate openings into arteries in the aortic arch. In particular, stent 10 may include fenestrations 53 that should be positioned in registry with their associated arteries as part of the proper placement of stent 10 in the aortic arch. Thus, in addition to adjusting a proper orientation of the sealing end of stent 10, the present disclosure may be utilized to adjust the positioning of the fenestrations with regard to their respective arteries to achieve both ideal sealing and ideal positioning as per the first image.

In all cases of implanting a stent 10 according to the present disclosure, the stent 10 is initially moved in a contracted configuration (FIG. 13, first image) toward a deployment area 62 in a passageway 60. Next, the stent 10 is changed from the contracted configuration 24 to a deployed configuration 25 in a first arrangement 71 with a wall 61 of the passageway 60, such as by withdrawing a sheath 74 that holds the stent 10 in a contracted configuration 24. Thereafter, after noting that the first arrangement 71 is less than desirable, the stent may be contracted from the deployed configuration 26 toward the contracted configuration 24 by immersing the stent 10 in an electromagnetic induction field 5. Thereafter, at least one of the orientation and position of the stent 10 is adjusted. Then, the stent may be expanded back to the deployed configuration 25 in a second arrangement 72, which is different than the first arrangement 71, with the wall 61 of the passageway 60 by ceasing the immersion of the stent 10 in the electromagnetic induction field 5 to allow the induction responsive muscles 30 to cool toward body temperature to allow the self expanding bias of the stent to dominate its shape. As discussed above, the stent 10 is contracted by changing the induction responsive muscles 30 from the relaxed state 31 to the contracted state 32. Likewise, the stent expands back to the deployed configuration 25 by changing the induction responsive muscles 30 from the contracted state 32 to the relaxed state 31 responsive to cooling due to the absence of the electromagnetic induction field 5. In all cases, the temperature of the induction responsive muscles 30 increase responsive to immersion in the electromagnetic induction field 5. This may occur directly, or indirectly through heating of the underlying material that makes up the tubular shaped framework 11. The adjustment of the position and/or orientation of the stent 10 may be performed by moving a deployment of device 70 that is connected to the stent. As shown, for instance in FIGS. 9-11, the adjustment may include merely adjusting an orientation of the stent 10. Also, the adjusting step may include changing the orientation of a sealing segment 29 of the stent as shown in FIG. 15. Or, the adjustment that may include changing a positioning of the sealing segment 29 in the passageway 60 as shown, for instance in FIG. 14. Also, the adjustment of the stent in general, and a sealing segment 29 in particular, may increase an area of contact between the sealing segment 29 and the wall of the passageway in the second arrangement 72 relative to the first arrangement 71.

An electromagnetic field generator 4 for generating an electromagnetic induction fields according to the present disclosure is well known and need not be taught again here. The present disclosure teaches an induction heating strategy that allows the diameter of a stent to be reduced after the stent has initially been fully expanded. Using this strategy, the physician can manipulate the stent 10 remotely, such as by using a deployment device, to readjust the stent's orientation, positioning or other irregularity (e.g. in-fold) if it initially landed sub-optimally. Thereafter, the strategy of the present disclosure may also be used to correct, for instance undesirable migration of a stent, as well as possibly assist in retracting a stent for removal from a patient.

The present description is for illustrative purposes only, and should not be construed to narrow the breadth of the present disclosure in any way. Thus, those skilled in the art will appreciate that various modification might be made to the presently disclosed embodiments without departing from the full and fair scope and spirit of the present disclosure. Other aspects, features and advantages will be apparent upon an examination of the attached drawings and appended claims.

What is claimed is:
1. A stent comprising:
a tubular shaped framework that includes a plurality of vertices that are each defined by a pair of struts;
a plurality of induction responsive artificial muscles, with each of the induction responsive artificial muscles being associated with one of the plurality of vertices by being attached to each strut of the pair of struts;
each of the induction responsive artificial muscles assuming a relaxed state at temperatures less than 37° C., and contracting toward a contracted state responsive to increasing the temperature to greater than 37° C.;
each of the induction responsive artificial muscles reducing an angle of a respective one of the vertices responsive to changing from the relaxed state to the contracted state; and
wherein a diameter of the tubular shaped framework is reduced responsive to a collective effect of the plurality of induction responsive artificial muscles changing from the relaxed state to the contracted state.

2. The stent of claim 1 including a fabric tube attached to the tubular shaped framework.

3. The stent of claim 1 wherein the plurality of induction responsive artificial muscles are out of contact with each other.

4. The stent of claim 1 wherein each of the induction artificial responsive muscles includes a spring that receives each strut of the pair of struts.

5. The stent of claim 1 wherein each of the induction responsive artificial muscles includes a living hinge.

6. The stent of claim 5 wherein each of the induction responsive artificial muscles includes the living hinge of a shape memory material attached to strut connecters of a material different from the shape memory material.

7. The stent of claim 1 wherein each of the induction responsive artificial muscles includes a bridge with one end attached to one strut of the pair of struts, and an opposite end attached to an other strut of the pair of struts.

8. The stent of claim 7 wherein the bridge includes exactly one bend between the one end and the opposite end.

9. The stent of claim 7 wherein the bridge includes a plurality of bends between the one end and the opposite end.

10. The stent of claim 1 including an artificial heart valve positioned within the tubular framework.

11. The stent of claim 1 including a fabric tube attached to the tubular shaped framework; and
   the fabric tube defines at least one fenestration.

12. The stent of claim 1 including a fabric tube attached to the tubular shaped framework; and
   the fabric tube defines exactly one entrance opening and defines exactly two exit openings.

13. The stent of claim 1 including a fabric tube attached to the tubular shaped framework; and
   a minority of a length of the fabric tube is a sealing segment; and
   the plurality of induction responsive muscles are in the sealing segment.

14. The stent of claim 1 including a fabric tube attached to the tubular framework;
   the tubular framework has a self-expanding bias toward a deployed configuration; and
   the induction responsive artificial muscles act in opposition to, and overcome, the self-expanding bias when being changed from the relaxed state to the contracted state.

* * * * *